United States Patent
Arigbamu

(10) Patent No.: US 10,667,783 B1
(45) Date of Patent: Jun. 2, 2020

(54) STETHOSCOPE WITH SOUND RECOGNITION CAPACITY

(71) Applicant: Samson Arigbamu, Baltimore, MD (US)

(72) Inventor: Samson Arigbamu, Baltimore, MD (US)

( * ) Notice: Subject to any disclaimer, the term of this patent is extended or adjusted under 35 U.S.C. 154(b) by 0 days.

(21) Appl. No.: 16/278,848

(22) Filed: Feb. 19, 2019

(51) Int. Cl.
| | |
|---|---|
| A61B 7/04 | (2006.01) |
| H04R 1/46 | (2006.01) |
| A61B 7/00 | (2006.01) |
| H04R 29/00 | (2006.01) |
| A61N 1/372 | (2006.01) |

(52) U.S. Cl.
CPC .............. *A61B 7/04* (2013.01); *H04R 1/46* (2013.01); *A61B 7/003* (2013.01); *A61N 1/37258* (2013.01); *H04R 29/004* (2013.01)

(58) Field of Classification Search
CPC .. A61B 7/04; A61B 7/003; H04R 1/46; H04R 29/004
See application file for complete search history.

(56) References Cited

U.S. PATENT DOCUMENTS

| | | | | |
|---|---|---|---|---|
| 1,543,453 A | * | 6/1925 | Smithline | A61B 7/02 181/137 |
| 4,783,813 A | | 11/1988 | Kempka | |
| 5,367,575 A | * | 11/1994 | Dieken | A61B 7/045 381/67 |
| 5,389,747 A | * | 2/1995 | Mohrin | A61B 7/02 181/131 |
| 5,737,429 A | | 4/1998 | Lee | |
| 5,774,563 A | * | 6/1998 | DesLauriers | A61B 7/026 381/67 |
| 5,825,895 A | * | 10/1998 | Grasfield | A61B 7/04 381/67 |
| 6,002,777 A | | 12/1999 | Grasfield | |
| 6,130,813 A | * | 10/2000 | Kates | H02H 9/001 307/80 |
| 6,520,924 B2 | * | 2/2003 | Lee | A61B 7/00 600/485 |
| 9,756,419 B2 | | 9/2017 | Renta | |
| 9,866,953 B2 | * | 1/2018 | Chong | H04R 1/46 |

(Continued)

FOREIGN PATENT DOCUMENTS

| | | | |
|---|---|---|---|
| CN | 2657587 Y | * | 11/2004 |
| WO | 2016206704 | | 12/2016 |

*Primary Examiner* — Davetta W Goins
*Assistant Examiner* — Kuassi A Ganmavo

(57) ABSTRACT

The stethoscope with sound recognition capacity is an electric stethoscope. The stethoscope with sound recognition capacity comprises a stethoscope and a sound processing device. The stethoscope is a traditional medical device used to listen for audible sounds inside a patient. The stethoscope of the stethoscope with sound recognition capacity performs this traditional function. The sound processing device is an electrical circuit housed within the stethoscope. The sound processing device: a) converts the audible sounds captured by the stethoscope into an electrical signal; b) processes the electrical signal to extract diagnostic information; c) processes the extracted diagnostic information to identify one or more conditions of diagnostic relevance found in the patient; and, d) makes an audible spoken announcement of the one or more conditions of diagnostic relevance.

12 Claims, 4 Drawing Sheets

(56) References Cited

U.S. PATENT DOCUMENTS

| | | | |
|---|---|---|---|
| 2008/0232604 A1* | 9/2008 | Dufresne | A61B 5/061 |
| | | | 381/67 |
| 2008/0298603 A1* | 12/2008 | Smith | A61B 7/026 |
| | | | 381/67 |
| 2011/0121783 A1* | 5/2011 | Boyles | H02J 7/0013 |
| | | | 320/113 |
| 2012/0271199 A1* | 10/2012 | Salisbury | A61B 5/4818 |
| | | | 600/586 |
| 2013/0119945 A1* | 5/2013 | Petersen | H02J 7/0052 |
| | | | 320/138 |
| 2015/0248536 A1* | 9/2015 | Tawil | G06Q 50/22 |
| | | | 705/3 |
| 2016/0296200 A1 | 10/2016 | Hinojosa | |
| 2018/0177484 A1 | 6/2018 | Habboushe | |

\* cited by examiner

US 10,667,783 B1

STETHOSCOPE WITH SOUND RECOGNITION CAPACITY

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary services including diagnosis and instruments for auscultation, more specifically, an electric stethoscope. (A61B7/04)

SUMMARY OF INVENTION

The stethoscope with sound recognition capacity is an electric stethoscope. The stethoscope with sound recognition capacity comprises a stethoscope and a sound processing device. The stethoscope is a traditional medical device used to listen for audible sounds inside a patient. The stethoscope of the stethoscope with sound recognition capacity performs this traditional function. The sound processing device is an electrical circuit housed within the stethoscope. The sound processing device: a) converts the audible sounds captured by the stethoscope into an electrical signal; b) processes the electrical signal to extract diagnostic information; c) processes the extracted diagnostic information to identify one or more conditions of diagnostic relevance found in the patient; and, d) makes an audible spoken announcement of the one or more conditions of diagnostic relevance.

These together with additional objects, features and advantages of the stethoscope with sound recognition capacity will be readily apparent to those of ordinary skill in the art upon reading the following detailed description of the presently preferred, but nonetheless illustrative, embodiments when taken in conjunction with the accompanying drawings.

In this respect, before explaining the current embodiments of the stethoscope with sound recognition capacity in detail, it is to be understood that the stethoscope with sound recognition capacity is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the stethoscope with sound recognition capacity.

It is therefore important that the claims be regarded as depart from the spirit and scope of the stethoscope with sound recognition capacity. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
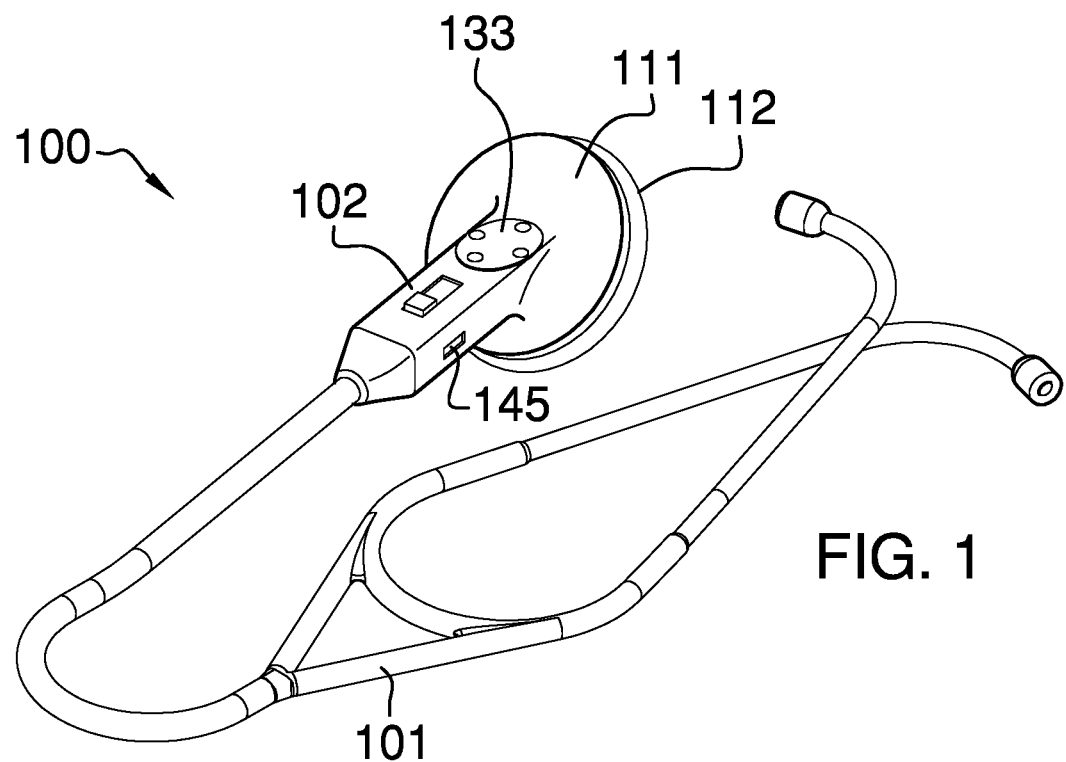
FIG. 1 is a perspective view of an embodiment of the disclosure.
Figure 2:
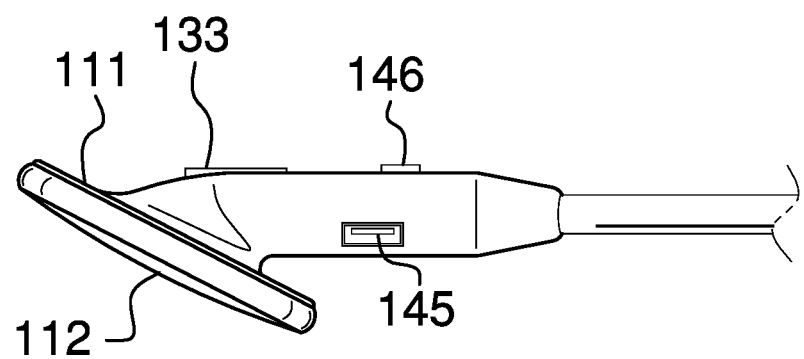
FIG. 2 is a side view of an embodiment of the disclosure.
Figure 3:
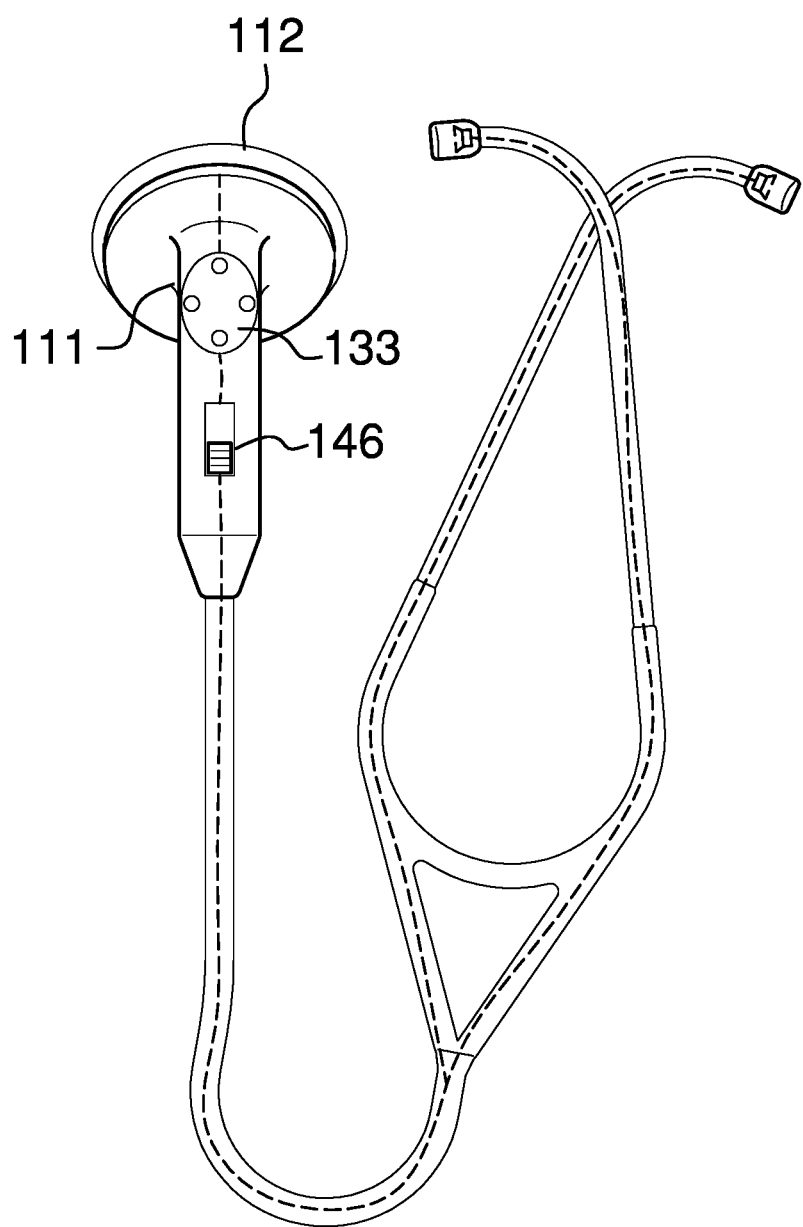
FIG. 3 is a top view of an embodiment of the disclosure.
Figure 4:
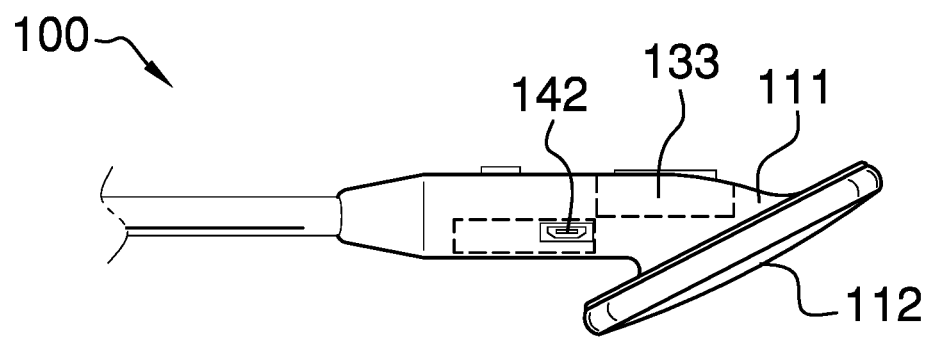
FIG. 4 is a reverse side view of an embodiment of the disclosure.
Figure 5:
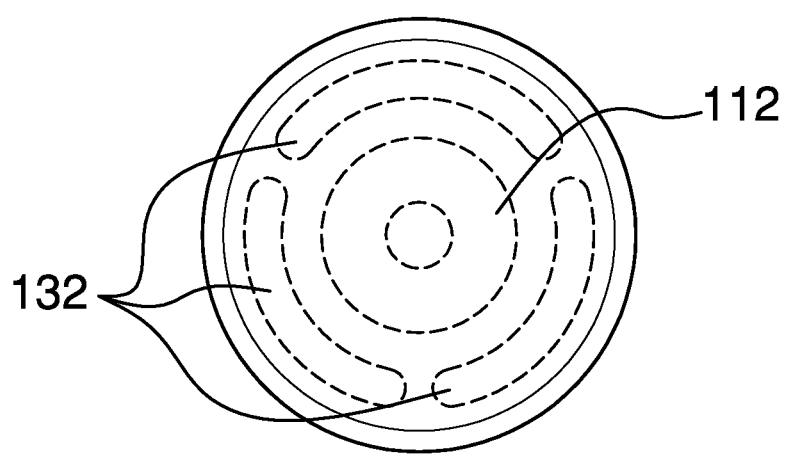
FIG. 5 is a detail view of an embodiment of the disclosure.
Figure 6:
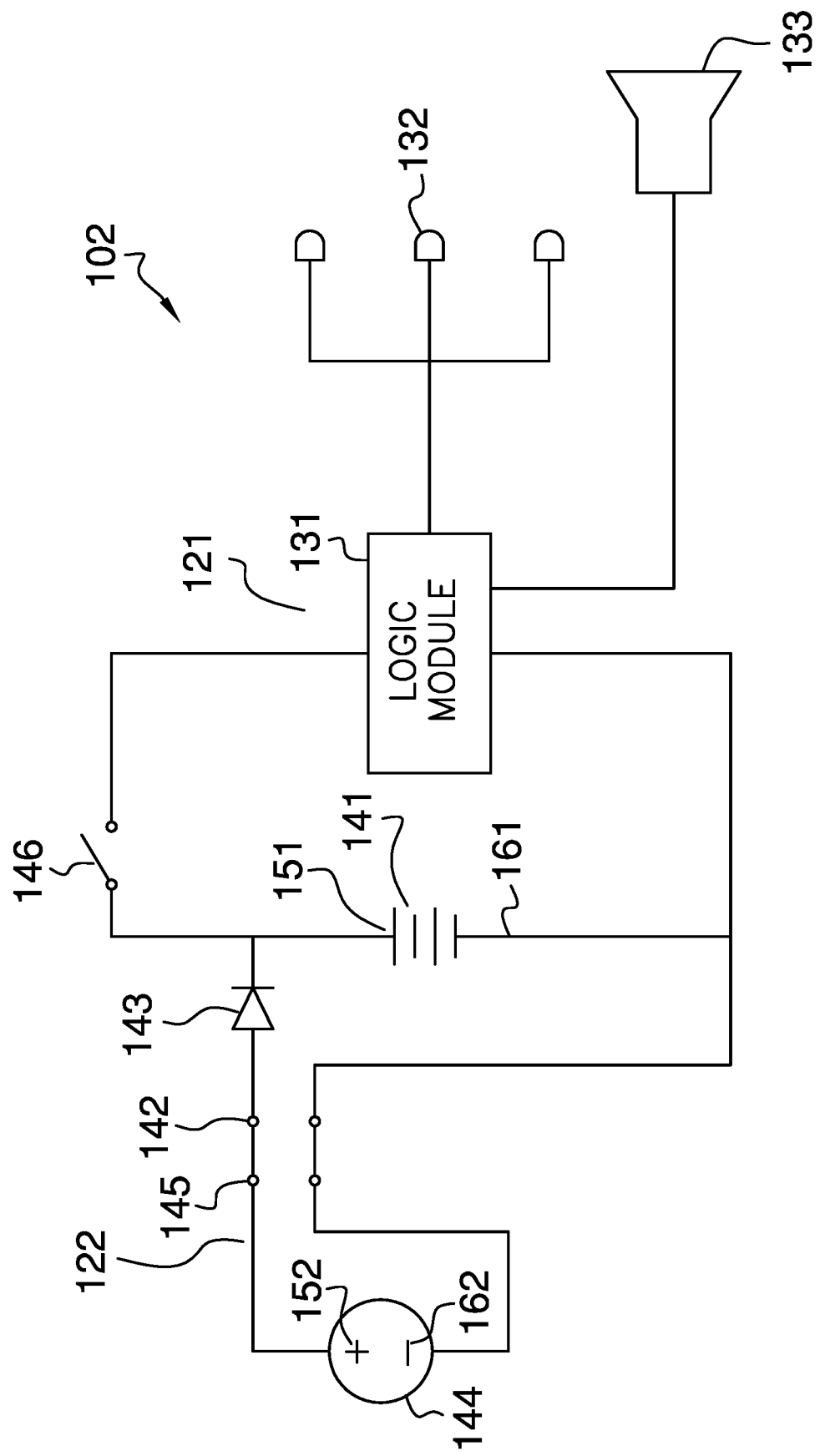
FIG. 6 is a block diagram of an embodiment of the disclosure.

Detailed reference will now be made to one or more potential embodiments of the disclosure, which are illustrated in FIGS. 1 through 6.

The stethoscope with sound recognition capacity 100 (hereinafter invention) is an electric stethoscope 101. The invention 100 comprises a stethoscope 101 and a sound processing device 102. The stethoscope 101 is a traditional medical device used to listen for audible sounds inside a patient. The function. The sound processing device 102 is an electrical circuit housed within the stethoscope 101. The sound processing device 102 converts the audible sounds captured by the stethoscope 101 into an electrical signal. The sound processing device 102 processes the electrical signal to extract diagnostic information. The sound processing device 102 processes the diagnostic information to identify one or more conditions of diagnostic relevance found in the patient. The sound processing device 102 makes an audible spoken announcement of the one or more conditions of diagnostic relevance.

The stethoscope 101 is a traditional medical device. The stethoscope 101 is used by a medical professional to listen for audible sounds in a patient. The stethoscope 101 is well-known and documented in the medical arts. The stethoscope 101 comprises a drum 111 and a diaphragm 112.

The drum 111 is a mechanical structure. The sound processing device 102 mounts in the drum 111. The drum 111 forms a chamber that transfers the audible sounds captured by the diaphragm 112 to the medical professional. The drum 111 is a hollow rigid structure. The drum 111 contains the sound processing device 102. The drum 111 is formed with all apertures and form factors necessary to allow the drum 111 to accommodate the use, the operation, and the external connections suitable for the purposes described in this disclosure are well-known and documented in the mechanical arts.

The diaphragm 112 is a sheeting. The diaphragm 112 mounts under tension over an aperture that leads into the chamber of the drum 111. The diaphragm 112 transfers any captured energy into the chamber of the drum 111. The diaphragm 112 mounts on the drum 111 in a manner similar to the mounting of a drum 111 skin on a musical percussion instrument known as a drum 111. The audible energy captured by the diaphragm 112 is converted into a vibration of the diaphragm 112.

The sound processing device 102 is an electrical circuit. The sound processing device 102 converts the audible sounds captured by the stethoscope 101 into an electrical signal. The sound processing device 102 processes the converted electrical signal to extract diagnostic information. The sound processing device 102 processes the extracted diagnostic information to identify one or more conditions of diagnostic relevance found in the patient. The sound processing device 102 makes an audible spoken announcement of the one or more conditions of diagnostic relevance found in the patient. The sound processing device 102 comprises a sound processing circuit 121 and a power circuit 122.

The sound processing circuit 121 is an electrical circuit. The sound processing circuit 121 processes the converted electrical signal received from the one or more microphones 132. The sound processing circuit 121 processes the extracted diagnostic information to identify one or more conditions of diagnostic relevance found in the patient. The sound processing circuit 121 is an audio device that makes an audible spoken announcement of the one or more conditions of diagnostic relevance found in the patient. The one or more conditions of diagnostic relevance announced by the sound processing circuit 121 are selected from a plurality of audio files previously stored on the sound processing circuit 121. The sound processing circuit 121 comprises a logic module 131, a one or more microphones 132, and a speaker 133.

The logic module 131 is a readily and commercially available programmable electronic device that is used to manage, regulate, and operate the sound processing device 102.

Each of the one or more microphones 132 is a transducer. Each of the one or more microphones 132 attaches to the diaphragm 112. Each of the one or more microphones 132 converts the vibrations of the diaphragm 112 into an electrical signal. The electrical signal generated by each of the one or more microphones 132 is transmitted to the sound processing circuit 121 for processing.

The speaker 133 is a transducer. The speaker 133 receives received electrical signal into audible sounds. The audible sounds generated by the speaker 133 are interpreted by listeners to be the audible spoken announcement of the one or more conditions of diagnostic relevance found in the patient.

The logic module 131 monitors the one or more microphones 132. The logic module 131 receives electrical signals generated by the one or more microphones 132. The logic module 131 processes the converted electrical signal received from the one or more microphones 132 to extract diagnostic information. The logic module 131 further processes the extracted diagnostic information to identify one or more conditions of diagnostic relevance found in the patient. The logic module 131 is the audio driver that generates the audible spoken announcement of the one or more conditions of diagnostic relevance found in the patient over the speaker 133. The logic module 131 further stores the audio files from which the audible spoken announcement of the one or more conditions of diagnostic relevance is selected.

The power circuit 122 is an electrochemical circuit. The power circuit 122 converts previously stored chemical potential energy into electrical energy used to operate the sound processing circuit 121. The power circuit 122 comprises a battery 141, a charging port 142, a diode 143, and an external first positive terminal 151 and a first negative terminal 161. The external power source 144 is further defined with a second positive terminal 152 and a second negative terminal 162.

The battery 141 is a commercially available rechargeable battery 141. The chemical energy stored within the rechargeable battery 141 is renewed and restored through use of the charging port 142. The charging port 142 is an electrical circuit that reverses the polarity of the rechargeable battery 141 and provides the energy necessary to reverse the chemical processes that the rechargeable battery 141 initially used to generate the electrical energy. This reversal of the chemical process creates a chemical potential energy that will later be used by the rechargeable battery 141 to generate electricity.

The charging port 142 attaches to an external power source 144 using a charging plug 145. The charging port 142 receives electrical energy from the external power source 144 through the charging plug 145. The charging plug 145 forms a detachable electrical connection with the charging port 142. The diode 143 is an electrical device that allows current to flow in only one direction. The diode 143 installs between the rechargeable battery 141 and the charging port 142 such that electricity will not flow from the first positive terminal 151 of the rechargeable battery 141 into the second positive terminal 152 embodiment of the disclosure, the external power source 144 and the charging port 142 are compatible with USB power requirements.

The power circuit 122 further comprises a master switch 146. The master switch 146 is a maintained switch electrically connected between the sound processing circuit 121 and the power circuit 122. The master switch 146 deactivates the sound processing circuit 121 such that the stethoscope 101 can be used in a traditional manner.

The following definitions were used in this disclosure:

Audio Device: As used in this disclosure, an audio device is a device that generates audible sound waves.

Audio File: As used in this disclosure, an audio file is a digital representation of a sound that is used to store a recording of the sound. Separate hardware is used to convert the digital representation of the sound into an audible sound.

Audio Source: As used in this disclosure, an audio source is a device that generates electrical signals that can be converted into audible sounds by a speaker.

Battery: As used in this disclosure, a battery is a chemical device consisting of one or more cells, in which chemical energy is converted into electricity and used as a source of power. Batteries are commonly defined with a positive terminal and a negative terminal.

Diaphragm: As used in this disclosure, a diaphragm refers to a sheeting placed under tension. A diaphragm is often used in mechanical and acoustic systems that generate, react to, or detect vibrational energy patterns.

Diode: As used in this disclosure, a diode is a two terminal semiconductor device that allows current flow in only one direction. The two terminals are called the anode and the cathode. Electric current is allowed to pass from the anode to the cathode.

External Power Source: As used in this disclosure, an external power source is a source of the energy that is externally provided to enable the operation of the present disclosure. Examples of external power sources include, but are not limited to, electrical power sources and compressed air sources.

Form Factor: As used in this disclosure, the term form factor refers to the size and shape of an object.

Housing: As used in this disclosure, a housing is a rigid casing that encloses and protects one or more devices.

Logic Module: As used in this disclosure, a logic module is a readily and commercially available electrical device that is programmable and that accepts digital and analog inputs, processes the digital and analog inputs according to previously stored instruction and provides the results of these instructions as digital or analog outputs.

Maintained Switch: A used in this disclosure, a maintained switch is a switch that maintains the position that was set in the most recent switch actuation. A maintained switch works in an opposite manner to a momentary switch.

Microphone: As used in this disclosure, a microphone is a transducer that converts the energy from vibration into electrical energy. The sources of vibrations include, but are not limited to, acoustic energy.

Patient: As used in this disclosure, a patient is a person who is designated to receive a medical treatment, therapy or service. The term patient may be extended to an animal when used within the context of the animal receiving veterinary treatment or services Plug: As used in this disclosure, a plug is an electrical termination that electrically connects a first electrical circuit to a second electrical circuit or a source of electricity. As used in this disclosure, a plug will have two or three metal pins.

Port: As used in this disclosure, a port is an electrical termination that is used to connect a first electrical circuit to a second external electrical circuit. In this disclosure, the port is designed to receive a plug.

Rigid Structure: As used in this disclosure, a rigid structure is a solid structure formed from an inelastic material that resists changes in shape. A rigid structure will permanently deform as it fails under a force.

Sensor: As used in this disclosure, a sensor is a device that receives and responds in a predetermined way to a signal or stimulus. As further used in this disclosure, a threshold sensor is a sensor that generates a signal that indicates whether the signal or stimulus is above or below a given threshold for the signal or stimulus.

Sheeting: As used in this disclosure, a sheeting is a material, such as a paper, textile, a plastic, or a metal foil, in the form of a thin flexible layer or layers.

Speaker: As used in this disclosure, a speaker is an electrical transducer that converts an electrical signal into an audible sound.

Stethoscope: As used in this disclosure, a stethoscope is an instrument that is used for listening to sounds within the body. A stethoscope further comprises a binaural, a binaural spring, a tube, a drum, and a diaphragm. The binaural, the binaural spring, and the tubing transports sound from the drum to the user. The drum and diaphragm detect the sounds within the body. The drum is a hollow chamber that attaches the diaphragm to the tubing. The diaphragm mounts under tension over the chamber of the drum. The diaphragm detects the acoustic energy generated by the body such that the acoustic energy captured by the diaphragm is transmitted into the chamber.

Switch: As used in this disclosure, a switch is an electrical device that starts and stops the flow of electricity through an electric circuit by completing or interrupting an electric circuit. The act of completing or breaking the electrical circuit is called actuation. Completing or interrupting an electric circuit with a switch is often referred to as closing or opening a switch respectively. Completing or interrupting an electric circuit is also often referred to as making or breaking the circuit respectively.

Tradition: As used in this disclosure, a tradition refers to: 1) a set of thoughts or expectations regarding a subject or object; or, 2) a method of using an object; that, 3) is perceived to be widely or commonly shared across a population of people; and, that, 4) is perceived to be widely or commonly shared across at least two generations within the population of people.

Transducer: As used in this disclosure, a transducer is a device that converts a physical quantity, such as pressure or brightness into an electrical signal or a device that converts an electrical signal into a physical quantity.

USB: As used in this disclosure, USB is an acronym for Universal Serial Bus which is an industry standard that defines the cables, the connectors, the communication protocols and the distribution of power required for interconnections between electronic devices. The USB standard defines several connectors including, but not limited to, USB-A, USB-B, mini-USB, and micro USB connectors. A USB cable refers to a cable that: 1) is terminated with USB connectors; and, 2) that meets the data transmission standards of the USB standard.

With respect to the above description, it is to be realized that the optimum dimensional relationship for the various components of the invention described above and in FIGS. 1 through 6 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. An electric stethoscope comprising:
   a stethoscope and a sound processing device;
   wherein the stethoscope is a traditional medical device;
   wherein the stethoscope captures audible sounds;
   wherein the sound processing device is an electrical circuit housed within the stethoscope;
   wherein the sound processing device converts the audible sounds captured by the stethoscope into an electrical signal;
   wherein the sound processing device converts the audible sounds captured by the stethoscope into an electrical signal;
   wherein the sound processing device processes the electrical signal to extract diagnostic information;

wherein the sound processing device processes the diagnostic information to identify one or more conditions of diagnostic relevance;
wherein the sound processing device makes an audible spoken announcement of the one or more conditions of diagnostic relevance;
wherein the sound processing device is an electrical circuit;
wherein the stethoscope comprises a drum and a diaphragm;
wherein the diaphragm is a sheeting;
wherein the drum is a mechanical structure;
wherein the drum forms a chamber that transfers the audible sounds captured by the diaphragm to the medical professional;
wherein the diaphragm transfers any captured energy into the chamber of the drum;
wherein the sound processing device comprises a sound processing circuit and a power circuit;
wherein the sound processing circuit is an electrical circuit;
wherein the power circuit is an electrochemical circuit;
wherein the sound processing circuit and the power circuit are electrically interconnected;
wherein the power circuit converts previously stored chemical potential energy into electrical energy used to operate the sound processing circuit;
wherein the sound processing circuit processes the converted electrical signal received from the one or more microphones;
wherein the sound processing circuit processes the extracted diagnostic information to identify one or more conditions of diagnostic relevance;
wherein the sound processing circuit is an audio device that makes the audible spoken announcement of the one or more conditions of diagnostic relevance;
wherein the diaphragm mounts under tension over an aperture that leads into the chamber of the drum;
wherein the sound processing device mounts in the drum;
wherein the audible energy captured by the diaphragm is converted into a vibration of the diaphragm.

2. The electric stethoscope according to claim 1 wherein the drum is a hollow rigid structure.

3. The electric stethoscope according to claim 1
wherein the sound processing circuit comprises a logic module, a one or more microphones, and a speaker;
wherein the logic module, the one or more microphones and the speaker are electrically interconnected.

4. The electric stethoscope according to claim 3
wherein the power circuit comprises a battery, a charging port, a diode, and an external power source;
wherein the battery, the charging port, the diode, and the external power source are electrically interconnected;
wherein the battery is further defined with a first positive terminal and a first negative terminal;
wherein the external power source is further defined with a second positive terminal and a second negative terminal.

5. The electric stethoscope according to claim 4
wherein each of the one or more microphones is a transducer;
wherein each of the one or more microphones attaches to the diaphragm;
wherein each of the one or more microphones converts the vibrations of the diaphragm into an electrical signal.

6. The electric stethoscope according to claim 5 wherein the electrical signal generated by each of the one or more microphones is transmitted to the sound processing circuit for processing.

7. The electric stethoscope according to claim 6
wherein the speaker is a transducer;
wherein the speaker receives electrical signals from the logic module and converts the received electrical signal into audible sounds;
wherein the audible sounds generated by the speaker are interpreted by listeners to be the audible spoken announcement of the one or more conditions of diagnostic relevance.

8. The electric stethoscope according to claim 7
wherein the logic module monitors the one or more microphones;
wherein the logic module receives electrical signals generated by the one or more microphones.

9. The electric stethoscope according to claim 8
wherein the logic module is a programmable electronic device;
wherein the logic module processes the converted electrical signal received from the one or more microphones to extract diagnostic information;
wherein the logic module further processes the extracted diagnostic information to identify one or more conditions of diagnostic relevance;
wherein the logic module is an audio driver that generates the audible spoken announcement of the one or more conditions of diagnostic relevance over the speaker.

10. The electric stethoscope according to claim 9
wherein the battery is a rechargeable battery;
wherein the charging port is an electrical circuit that reverses the polarity of the rechargeable battery;
wherein the charging port attaches to the external power source using a charging plug;
wherein the charging plug forms a detachable electrical connection with the charging port;
wherein the charging port receives electrical energy from the external power source through the charging plug.

11. The electric stethoscope according to claim 10
wherein the power circuit further comprises a master switch;
wherein the master switch is a maintained switch that electrically connects between the sound processing circuit and the power circuit;
wherein the master switch deactivates the sound processing circuit.

12. The electric stethoscope according to claim 11
wherein the diode is an electrical device that allows current to flow in only one direction;
wherein the diode installs between the rechargeable battery and the charging port such that electricity will not flow from the first positive terminal of the rechargeable battery into the second positive terminal of the external power source.

* * * * *